United States Patent [19]

Nakano et al.

[11] Patent Number: 5,948,938
[45] Date of Patent: Sep. 7, 1999

[54] PROCESS FOR PREPARING N-PHOSPHONOMETHYLGLYCINE

[75] Inventors: Kunio Nakano, Kawasaki; Shuzi Sayama, Yamato; Yukio Hirayama, Kawasaki; Naohiko Ohashi, Tokyo, all of Japan

[73] Assignee: Sankyo Company, Limited, Tokyo, Japan

[21] Appl. No.: 08/944,029

[22] Filed: Aug. 29, 1997

Related U.S. Application Data

[63] Continuation of application No. PCT/JP96/00550, Mar. 7, 1996.

[30] Foreign Application Priority Data

Mar. 7, 1995 [JP] Japan ..................................... 7-046005

[51] Int. Cl.$^6$ ....................................................... C07F 9/22
[52] U.S. Cl. ............................................................... 562/17
[58] Field of Search .............................. 562/17; 558/169, 558/166

[56] References Cited

U.S. PATENT DOCUMENTS

| | | |
|---|---|---|
| 4,397,676 | 8/1983 | Bakel . |
| 4,486,356 | 12/1984 | Bakel . |
| 4,624,937 | 11/1986 | Chou . |
| 5,043,475 | 8/1991 | Fields, Jr. ................................. 567/17 |

*Primary Examiner*—Gary Geist
*Assistant Examiner*—Brian J. Davis
*Attorney, Agent, or Firm*—Frishauf, Holtz, Goodman, Langer & Chick, P.C.

[57] ABSTRACT

A process for preparing N-phosphonomethylglycine, which comprises treating N-phosphonomethyliminodiacetic acid in the presence of water, activated carbon and hydrogen peroxide. This process is a safe and efficient process for preparing N-phosphonomethylglycine.

28 Claims, No Drawings

PROCESS FOR PREPARING N-PHOSPHONOMETHYLGLYCINE

This application is a continuation application of International Application PCT/JP96/00550 filed Mar. 7, 1996.

This invention relates to an improved process for preparing N-phosphonomethylglycine which has been utilized as a starting material or an intermediate of a N-phosphonomethylglycine salt which has widely been used as a herbicide.

BACKGROUND OF THE INVENTION

A number of processes for preparing N-phosphonomethylglycine (hereinafter abbreviated to PMG) using N-phosphonomethyliminodiacetic acid (hereinafter abbreviated to PMIDA) as a starting material, using water as a solvent and using an oxidizing agent and a catalyst may be mentioned. Among them:

(a) a process in which, under ordinary pressure or under high pressure, molecular oxygen or gas containing said oxygen is used as an oxidizing agent and activated carbon is used as a catalyst is found in (1) Japanese Unexamined Patent Publication (KOKAI) No. Sho 50-160222, (2) Japanese Unexamined Patent Publication (KOKAI) No. Sho 56-18994 and (3) Japanese Unexamined Patent Publication (KOKAI) No. Sho 60-246328, (b) a process in which hydrogen peroxide is used as an oxidizing agent and an acid (an organic acid or an inorganic acid) is used as a catalyst is found in (4) Japanese Unexamined Patent Publication (KOKAI) No. Sho 49-48620 and (5) Japanese Unexamined Patent Publication (KOKAI) No. Hei 2-270891, and (c) a process in which hydrogen peroxide is used as an oxidizing agent and a metal compound is used as a catalyst is found in (6) Japanese Unexamined Patent Publication (KOKAI) No. Hei 4-224593, (7) Japanese Unexamined Patent Publication (KOKAI) No. Hei 4-210992, (8) Japanese Unexamined Patent Publication (KOKAI) No. Hei 4-224592 and (9) Japanese Unexamined Patent Publication (KOKAI) No. Hei 4-273885, respectively.

In the technique of (a), the reaction proceeds extremely slowly under ordinary pressure, whereas although the yield of the reaction is good under high pressure, pressure equipment is required. Further, it is necessary to pre-treat the activated carbon to be used. For these reasons, this technique leads to increase in cost.

In the technique of (b), an organic acid or an inorganic acid is used, so that the reaction apparatus might be corroded, and much time is required for disposal of the used acid.

In the technique of (c), a metal compound is used. Some metal compounds are harmful substances, so that disposal might be attended by difficulties or, when the possibility of contaminating the product PMG with a harmful catalyst is considered, a countermeasure should be taken in view of environmental problems.

Since the problems as described above are involved, it has been demanded to develop a safe and efficient preparation process.

DISCLOSURE OF THE INVENTION

The present inventors have intensively studied a process which can solve the above problems and consequently PMG can be obtained safely and efficiently by treating PMIDA in the presence of water, activated carbon and hydrogen peroxide, to accomplish the present invention.

This finding is surprising. This is because it appears easy to achieve the present invention by selecting hydrogen peroxide as an oxidizing agent and activated carbon as a catalyst if the above prior techniques (a) and (b) are combined, but it has been believed in this field of the art that it is impossible to make such a selection.

That is, it has widely been known that activated carbon has a catalytic action in the decomposition of hydrogen peroxide and has been used as a reaction terminator. For example, there may be mentioned a technical book "Activated Carbon [written by John W. Hustler, translated by Takashi Oda and Yoshitomo Eguchi, page 220, line 2 to line 4 (Kyoritsu Shuppan Co.), Mar. 15, 1978, the third edition, the second impression]" or Japanese Unexamined Patent Publication (KOKAI) No. Sho 58-219193. In particular, in said patent publication (Example 6, page 9, lower left column, line 5), in preparation of a PMG guanidine salt, after hydrogen peroxide ($H_2O_2$) is added to a PMIDA guanidine salt to complete the reaction, activated carbon is added to the reaction mixture to decompose excess hydrogen peroxide. That is, it is described that activated carbon was used as a reaction terminator.

Therefore, if hydrogen peroxide and activated carbon are made to co-exist particularly under heating, hydrogen peroxide is immediately decomposed into water and oxygen, so that even if this system is applied to PMIDA, i.e., since this system belongs to the prior technique of the above (a), it could not be considered by a person skilled in the art to employ such a circuitous and disadvantageous process which is inferior to the process (a) even by using hydrogen peroxide and activated carbon. On the other hand, it has been found that when PMIDA is reacted under atmospheric pressure by using oxygen and activated carbon, the reaction proceeds extremely slowly, and the yield of PMG is low. However, it has been found unexpectedly that when PMIDA is reacted under atmospheric pressure by using hydrogen peroxide and activated carbon, the reaction proceeds extremely rapidly, and the desired PMG can be obtained in high yield. Not only it could not be supposed to employ such a combination, but also effects brought about by the combination are also quite unexpected.

It has been estimated that in the process of the present invention, since hydrogen peroxide and activated carbon are used, the following two stage reactions proceed.

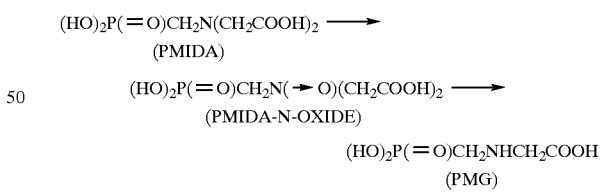

However, actually, in the reaction of PMIDA and hydrogen peroxide, almost no PMIDA-N-oxide is detected during the reaction, and even when separately synthesized PMIDA-N-oxide is treated in the presence of activated carbon, almost no PMG is produced. Therefore, it is not certain whether PMG is produced by the above two stage reactions or not.

Anyway, it is estimated that in the present invention, hydrogen peroxide and PMIDA are activated by activated carbon to be easily converted into PMG.

In the following, the present invention is explained in more detail.

BEST MODE FOR PRACTICING THE INVENTION

PMIDA which is a starting material of the present invention can be prepared by a process well known in this field of the art, for example, reaction of formaldehyde, iminodiacetic acid and orthophosphorous acid in the presence of sulfuric acid (Japanese Unexamined Patent Publication (KOKAI) No. Sho 49-48620), a process in which iminodiacetic acid is reacted with formaldehyde and phosphorous acid in the presence of hydrochloric acid (Japanese Unexamined Patent Publication (KOKAI) No. Sho 50-160222) or a process in which phosphorus trichloride is added to an aqueous sodium iminodiacetate solution and the mixture is reacted with formaldehyde (Japanese Patent Publication (KOKOKU) No. Hei 5-37431). PMIDA to be provided for the present invention may be prepared by a process other than the above processes and is not particularly limited.

As the activated carbon to be used in the present invention, there may be used generally commercially available various kinds of activated carbons. Many kinds of activated carbons are commercially available. For example, when the activated carbons are classified according to a starting material, there may be mentioned activated carbons such as peat carbon using peat as a starting material, lignite carbon using brown coal or lignite as a starting material, coal carbon using bituminous coal or the like as a starting material, wood carbon and woody carbon using wood or a woody material as a starting material and coconut shell carbon using coconut shell as a starting material. Further, when they are classified according to a shape, there may be mentioned granulated carbon, granular carbon, pulverized carbon, powdered carbon, etc.

Examples of the activated carbon to be used in the present invention are shown below, but all of them cannot be shown. However, the activated carbon should not be limited thereto as a matter of course.

Granular Shirasagi Gc, Granular Shirasagi Cc, Granular Shirasagi Wc, Granular Shirasagi WHc, Granular Shirasagi LHc, Granular Shirasagi WHA, Granular Shirasagi GOC, Granular Shirasagi APRC, Granular Shirasagi TAC, Granular Shirasagi MAC, Granular Shirasagi XRC and Granular Shirasagi NCC, Granular Shirasagi KL, Granular Shirasagi DC, Granular Shirasagi Gx, Granular Shirasagi Sx, Granular Shirasagi Cx, X-7000, X-7100, Granular Shirasagi GHx, Granular Shirasagi GHxUG, Granular Shirasagi GS1x, Granular Shirasagi GS2x, Granular Shirasagi GTx, Granular Shirasagi GTSx, Granular Shirasagi Gx, Granular Shirasagi SRCx, MOLSIEVON 3A, MOLSIEVON 4A, MOLSIEVON 5A and ALDENITE, CARBORAFFIN, High Power Shirasagi, Purified Shirasagi, Special Shirasagi, Shirasagi A, Shirasagi M, Shirasagi C, Shirasagi P and Shirasagi PHC which are produced by Takeda Chemical Industries, Ltd.

BM-WA, BM-WD, BM-AL, BM-AH, BM-GB, BM-GA, BM-GCA, MM-CD, MM-CB, MM-CBS, GM-GB, GM-GA, GM-GH, GM-AS, GM-AA, PM-PA, PM-PW, PM-PW1, PM-WA, PM-KI, PM-YO, PM-KS, PM-MO, PM-AA, PM-PE, PM-CR, PM-WA, PM-SX, PM-FZ and PM-SAY which are produced by Mitsui Pharmaceuticals, Inc.

CAL, CPG, SGL, FILTRASORB 300, FILTRASORB 400, CANE CAL, APC, BPL, PCB, IVP, HGR, CP-4, FCA and Granular AL which are produced by Toyo Calgon Co.

Kuraraycoal GG, Kuraraycoal GS, Kuraraycoal GC, Kuraraycoal SA, Kuraraycoal KG, Kuraraycoal GM, Kuraraycoal GW, Kuraraycoal GL, Kuraraycoal GLC, Kuraraycoal KW, Kuraraycoal GWC, Kuraraycoal PW, Kuraraycoal PW-W5, Kuraraycoal PK, Kuraraycoal YP, Kuraraycoal T-B, Kuraraycoal G-H, Kuraraycoal T-S, Kuraraycoal T-F and Kuraraycoal T-C which are produced by Kuraray Chemical Co.

Taiko TA, Taiko TS, Taiko TG, Taiko TM, Taiko GL30, Taiko GL30A, Taiko GF30A, Taiko GF50A, Taiko CW1303, Taiko CW130BR, Taiko CW130A, Taiko CW130AR, Taiko CW612G, Taiko CW816G, Taiko CG48B, Taiko CG48BR, Taiko CG48A, Taiko CG48AR, Taiko SG, Taiko SGP, Taiko SGA, Taiko S, Taiko FC, Taiko FCS, Taiko SA1000, Taiko K, Taiko KS, Taiko KW-50, Taiko K(A), Taiko A, Taiko M, Taiko AP, Taiko RC, Taiko B5, Taiko P and Taiko W which are produced by Futamura Chemical Industry Co.

Tsurumicoal 4GS-S, Tsurumicoal 4G-2S, Tsurumicoal 4G-3S, Tsurumicoal 7GM, Tsurumicoal 4GM, Tsurumicoal 4GCX, Tsurumicoal SX, Tsurumicoal AX, Tsurumicoal MX, Tsurumicoal GOD, Tsurumicoal 4GM-X, Tsurumicoal 4GS-D, Tsurumicoal HC-6, Tsurumicoal HC-14, Tsurumicoal HC-20, Tsurumicoal HC-20C, Tsurumicoal HCA-S, Tsurumicoal 5GV, Tsurumicoal 4GV, Tsurumicoal GVA-S, Tsurumicoal HC-42, Tsurumicoal HC-30E, Tsurumicoal GL-30, Tsurumicoal HC-30X, Tsurumicoal 4GL, Tsurumicoal HC-30S, Tsurumicoal GL-30S, Tsurumicoal PA and Tsurumicoal PC which are produced by Tsurumi Coal Co.

NORIT PK, NORIT PKDA 10×30 MESH, NORIT ELORIT, NORIT AZO, NORIT GRANULAR DARCO, NORIT HYDRO DARCO, NORIT DARCO 8×30, NORIT DARCO 12×20 LI, NORIT DARCO 12×20 DC, NORIT PETRO DARCO, NORIT DARCO MRX, NORIT HYDRODARCO GCW, NORIT HYDRODARCO GCL, NORIT HYDRODARCO GTS, NORIT DARCO CF, NORIT DARCO VAPURE, NORIT DARCO GCV, NORIT C-GRANULAR, NORIT ROW, NORIT ROW 0.8 SUPRA, NORIT RO, NORIT ROX, NORIT ROX 0.8, NORIT RB, NORIT R, NORIT R. Extra, NORIT Sorbonorit, NORIT CAR, NORIT ROZ, NORIT RBAA, NORIT RBHG, NORIT RZN, NORIT RGM, NORIT SX, NORIT SX-ULTRA, NORIT SA, NORIT SA-1, NORIT D-10, NORIT PN, NORIT ZN, NORIT SA-AW, NORIT W, NORIT GL, NORIT CA, NORIT CA-1, NORIT CA-SP, NORIT CN, NORIT CG, NORIT DARCO KB, NORIT DARCO KBB, NORIT S-51, NORIT DARCO S-51, NORIT S-51-A, NORIT S-51FF, NORIT PREMIUM DARCO, NORIT DARCO GFP, NORIT HDC, NORIT HDR, NORIT HDH, NORIT GRO SAFE, NORIT FM-1, NORIT DARCO TRS and NORIT DARCO FGD which are available from Nippon Norit Co.

The amount of the activated carbon to be used may be 0.1 part by weight or more, preferably 0.1 to 0.75 part by weight, most preferably 0.1 to 0.4 part by weight based on 1 part by weight of PMIDA. If the amount is less than 0.1 part by weight, the reaction is not completed, and further side reaction occurs to lower purity, whereby the object of the present invention cannot be achieved. If it exceeds 0.75 part by weight, bad influence is not particularly exerted on quality and yield, but an effect to be brought about by use thereof cannot be expected, and it is not economical. The object can be achieved by powdery activated carbon in a smaller amount as compared with granular activated carbon.

The great characteristic of the activated carbon to be used in the present invention resides in that after it is used in the first reaction and recovered, it can be recycled as such any number of times for the second reaction and reactions subsequent thereto without regeneration treatment such as activation. When the activated carbon is used repeatedly, its activity as a catalyst is not lowered, which is extremely economical. When the activated carbon is lost in operation such as filtration by using the activated carbon repeatedly, the lost amount thereof may be replenished.

As the hydrogen peroxide to be used in the present invention, a generally commercially available 30 to 60% by weight aqueous solution may be used, and it is not necessary to further dilute the solution with water.

The amount of the hydrogen peroxide to be used may be 2 moles or more, preferably 2 to 5 moles, most preferably 2.0 to 2.5 moles based on 1 mole of PMIDA. If the amount is less than 2 moles, the reaction is not completed, and a large amount of PMIDA remains as an unreacted compound. If it exceeds 5 moles, bad influence is not particularly exerted on quality and yield, but an effect to be brought about by use thereof cannot be expected and it is not economical.

The reaction of PMIDA and hydrogen peroxide in the present invention is an exothermic reaction, and the time of adding hydrogen peroxide varies depending on the cooling performance of the equipment, but it may be in the range which can remove the heat of reaction. The reaction proceeds rapidly by adding hydrogen peroxide, so that a long reaction time is not required and it is easy to control the reaction. The end point of said reaction can be determined by monitoring disappearance of PMIDA. The reaction of the present invention is completed in about 30 minutes to about 4 hours if the cooling performance of the reaction equipment is sufficient.

The reaction in the present invention proceeds in the presence of water. The amount of water may be any amount so long as the reaction mixture can be stirred. It may not be an amount which is sufficient for dissolving PMIDA or PMG and is not particularly limited. In general, it may be 1 part by weight or more, preferably 2 to 10 parts by weight based on 1 part by weight of PMIDA.

The reaction temperature in the present invention is preferably 50 to 90° C., and a further preferred temperature range is 60 to 80° C. If the temperature is 50° C. or lower, the progress of the reaction is slow, while if it exceeds 90° C., a by-product is produced to lower the purity and yield of the desired compound.

The pressure for practicing the present invention is not particularly limited so long as it is in the range for achieving the object of the present invention, and the present invention is practiced under pressure lower than atmospheric pressure, atmospheric pressure or pressure higher than atmospheric pressure. However, it is not particularly necessary to practice the present invention under pressure lower than atmospheric pressure or pressure higher than atmospheric pressure, and atmospheric pressure is sufficient. It is not necessary to use an expensive and dangerous autoclave requiring complicated operation, which is necessary in a process in which activated carbon and oxygen-containing gas are used in combination.

In the present invention, depending on the amount of water used, after completion of the reaction, the produced PMG is precipitated in a crystalline state or is dissolved to give an aqueous solution. There are various methods for isolating PMG as crystals, and there may be mentioned, for example, the following operation methods.

Isolation method (A): When the amount of water used is more than an amount which is necessary for dissolving the produced PMG, for example, the amount is 15 times by weight or more the amount of the charged PMIDA, the reaction mixture is heated to suitable temperature or higher, for example, 80° C. or higher, preferably 85 to 90° C. and filtered under heating to separate activated carbon by filtration. The filtrate is concentrated under reduced pressure to an amount of suitable times, for example, 3.5 times by weight the amount of the charged PMIDA to isolate PMG crystals by crystallization.

Isolation method (B): When the amount of water used is less than an amount which is necessary for dissolving the produced PMG, for example, the amount is less than 15 times by weight the amount of the charged PMIDA, the reaction mixture is cooled to low temperature, for example, about 5° C., and the precipitated PMG and activated carbon are separated by filtration. A mixed cake comprising these PMG crystals and the activated carbon is dissolved in hot water, for example, at 80° C. or higher, preferably 85 to 90° C. in an amount of suitable times, for example, 15 times by weight the amount of the charged PMIDA. Thereafter, the solution is filtered under heating to separate the activated carbon by filtration. The filtrate is concentrated under reduced pressure to an amount of suitable times, for example, 3.5 times by weight the amount of the charged PMIDA to isolate PMG crystals by crystallization.

Isolation method (C): In Isolation method (A) and Isolation method (B), filtration under heating is carried out to separate activated carbon by filtration, whereby a filtrate is obtained. To the filtrate is added a water-soluble organic solvent, for example, methanol, acetone or acetonitrile in an amount of suitable times or more, for example, once by volume or more the amount of the filtrate to isolate PMG crystals by crystallization. In Isolation method (C), the yield is increased by several % as compared with Isolation method (A) or Isolation method (B).

Isolation method (D): After completion of the reaction, to the reaction mixture is added an inorganic base, for example, alkali hydroxide, preferably sodium hydroxide, or an organic base, for example, an organic amine such as isopropylamine in an amount which is sufficient for producing a salt by reaction with the produced PMG to form a PMG salt, whereby an aqueous solution of the PMG salt is prepared. The solution is filtered to separate activated carbon by filtration, and the filtrate is made acidic with a mineral acid or the like to isolate PMG by crystallization.

PMG to be obtained by the process of the present invention is obtained at high levels of purity and yield which are satisfactory values as an industrial preparation process.

For practicing the present invention, there may be mentioned the following embodiments.

(1) A process for preparing PMG by adding hydrogen peroxide to PMIDA, water and activated carbon while heating and stirring them.

(2) A process for preparing PMG by adding 2 to 5 moles of hydrogen peroxide based on 1 mole of PMIDA to PMIDA, water and activated carbon while heating and stirring them.

(3) A process for preparing PMG by adding 2.0 to 2.5 moles of hydrogen peroxide based on 1 mole of PMIDA to PMIDA, water and activated carbon while heating and stirring them.

(4) A process for preparing PMG by adding hydrogen peroxide to 1 part by weight of PMIDA, 0.1 to 0.75 part by weight of activated carbon and water while heating and stirring them.

(5) A process for preparing PMG by adding 2 to 5 moles of hydrogen peroxide based on 1 mole of PMIDA to 1 part by weight of PMIDA, 0.1 to 0.75 part by weight of activated carbon and water while heating and stirring them.

(6) A process for preparing PMG by adding 2.0 to 2.5 moles of hydrogen peroxide based on 1 mole of PMIDA to 1 part by weight of PMIDA, 0.1 to 0.75 part by weight of activated carbon and water while heating and stirring them.

(7) A process for preparing PMG by adding hydrogen peroxide to 1 part by weight of PMIDA, 0.1 to 0.4 part by weight of activated carbon and water while heating and stirring them.

(8) A process for preparing PMG by adding 2 to 5 moles of hydrogen peroxide based on 1 mole of PMIDA to 1 part by weight of PMIDA, 0.1 to 0.4 part by weight of activated carbon and water while heating and stirring them.

(9) A process for preparing PMG by adding 2.0 to 2.5 moles of hydrogen peroxide based on 1 mole of PMIDA to 1 part by weight of PMIDA, 0.1 to 0.4 part by weight of activated carbon and water while heating and stirring them.

(10) A process for preparing PMG by adding hydrogen peroxide to PMIDA, water and recovered activated carbon while heating and stirring them.

(11) A process for preparing PMG by adding 2 to 5 moles of hydrogen peroxide to 1 mole of PMIDA, water and recovered activated carbon while heating and stirring them.

(12) A process for preparing PMG by adding 2.0 to 2.5 moles of hydrogen peroxide to 1 mole of PMIDA, water and recovered activated carbon while heating and stirring them.

(13) A process for preparing PMG by adding hydrogen peroxide to 1 part by weight of PMIDA, 0.1 to 0.75 part by weight of recovered activated carbon and water while heating and stirring them.

(14) A process for preparing PMG by adding 2 to 5 moles of hydrogen peroxide based on 1 mole of PMIDA to 1 part by weight of PMIDA, 0.1 to 0.75 part by weight of recovered activated carbon and water while heating and stirring them.

(15) A process for preparing PMG by adding 2.0 to 2.5 moles of hydrogen peroxide based on 1 mole of PMIDA to 1 part by weight of PMIDA, 0.1 to 0.75 part by weight of recovered activated carbon and water while heating and stirring them.

(16) A process for preparing PMG by adding hydrogen peroxide to 1 part by weight of PMIDA, 0.1 to 0.4 part by weight of recovered activated carbon and water while heating and stirring them.

(17) A process for preparing PMG by adding 2 to 5 moles of hydrogen peroxide based on 1 mole of PMIDA to 1 part by weight of PMIDA, 0.1 to 0.4 part by weight of recovered activated carbon and water while heating and stirring them.

(18) A process for preparing PMG by adding 2.0 to 2.5 moles of hydrogen peroxide based on 1 mole of PMIDA to 1 part by weight of PMIDA, 0.1 to 0.4 part by weight of recovered activated carbon and water while heating and stirring them.

(19) A process for preparing PMG by adding hydrogen peroxide to PMIDA, water and activated carbon under atmospheric pressure while heating and stirring them.

(20) A process for preparing PMG by adding 2 to 5 moles of hydrogen peroxide to 1 mole of PMIDA, water and activated carbon under atmospheric pressure while heating and stirring them.

(21) A process for preparing PMG by adding 2.0 to 2.5 moles of hydrogen peroxide to 1 mole of PMIDA, water and activated carbon under atmospheric pressure while heating and stirring them.

(22) A process for preparing PMG by adding hydrogen peroxide to 1 part by weight of PMIDA, 0.1 to 0.75 part by weight of activated carbon and water under atmospheric pressure while heating and stirring them.

(23) A process for preparing PMG by adding 2 to 5 moles of hydrogen peroxide based on 1 mole of PMIDA to 1 part by weight of PMIDA, 0.1 to 0.75 part by weight of activated carbon and water under atmospheric pressure while heating and stirring them.

(24) A process for preparing PMG by adding 2.0 to 2.5 moles of hydrogen peroxide based on 1 mole of PMIDA to 1 part by weight of PMIDA, 0.1 to 0.75 part by weight of activated carbon and water under atmospheric pressure while heating and stirring them.

(25) A process for preparing PMG by adding hydrogen peroxide to 1 part by weight of PMIDA, 0.1 to 0.4 part by weight of activated carbon and water under atmospheric pressure while heating and stirring them.

(26) A process for preparing PMG by adding 2 to 5 moles of hydrogen peroxide based on 1 mole of PMIDA to 1 part by weight of PMIDA, 0.1 to 0.4 part by weight of activated carbon and water under atmospheric pressure while heating and stirring them.

(27) A process for preparing PMG by adding 2.0 to 2.5 moles of hydrogen peroxide based on 1 mole of PMIDA to 1 part by weight of PMIDA, 0.1 to 0.4 part by weight of activated carbon and water under atmospheric pressure while heating and stirring them.

(28) A process for preparing PMG by adding hydrogen peroxide to PMIDA, water and recovered activated carbon under atmospheric pressure while heating and stirring them.

(29) A process for preparing PMG by adding 2 to 5 moles of hydrogen peroxide to 1 mole of PMIDA, water and recovered activated carbon under atmospheric pressure while heating and stirring them.

(30) A process for preparing PMG by adding 2.0 to 2.5 moles of hydrogen peroxide to 1 mole of PMIDA, water and recovered activated carbon under atmospheric pressure while heating and stirring them.

(31) A process for preparing PMG by adding hydrogen peroxide to 1 part by weight of PMIDA, 0.1 to 0.75 part by weight of recovered activated carbon and water under atmospheric pressure while heating and stirring them.

(32) A process for preparing PMG by adding 2 to 5 moles of hydrogen peroxide based on 1 mole of PMIDA to 1 part by weight of PMIDA, 0.1 to 0.75 part by weight of recovered activated carbon and water under atmospheric pressure while heating and stirring them.

(33) A process for preparing PMG by adding 2.0 to 2.5 moles of hydrogen peroxide based on 1 mole of PMIDA to 1 part by weight of PMIDA, 0.1 to 0.75 part by weight of recovered activated carbon and water under atmospheric pressure while heating and stirring them.

(34) A process for preparing PMG by adding hydrogen peroxide to 1 part by weight of PMIDA, 0.1 to 0.4 part by weight of recovered activated carbon and water under atmospheric pressure while heating and stirring them.

(35) A process for preparing PMG by adding 2 to 5 moles of hydrogen peroxide based on 1 mole of PMIDA to 1 part by weight of PMIDA, 0.1 to 0.4 part by weight of recovered activated carbon and water under atmospheric pressure while heating and stirring them.

(36) A process for preparing PMG by adding 2.0 to 2.5 moles of hydrogen peroxide based on 1 mole of PMIDA to 1 part by weight of PMIDA, 0.1 to 0.4 part by weight of recovered activated carbon and water under atmospheric pressure while heating and stirring them.

As a preferred embodiment of the present invention, there may be mentioned the preparation processes of the above embodiments (2), (3), (5), (6), (8), (9), (11), (12), (14), (15), (17), (18), (20), (21), (23), (24), (26), (27), (29), (30), (32), (33), (35) and (36), and as the most preferred embodiment, there may be mentioned the preparation processes of the embodiments (9), (18), (27) and (36).

EXAMPLES

In the following, Examples of the process of the present invention are shown, but the present invention is not limited thereto. The net amount of PMG obtained (Net) shows a value calculated from the gross amount of crystals obtained by isolation (Gross)×purity (the content of PMG), the yield shows a value calculated from (the net amount of PMG obtained/the theoretical value of PMG obtained)×100, and the conversion rate shows a value calculated from (the content of the produced PMG (molar number)/the amount of the used starting material PMIDA (molar number))×100, respectively. The content of PMG was quantified by high performance liquid chromatography (HPLC).

Example 1

To 100 ml of water were added 5 g of the activated carbons shown in Table 1 and 20.0 g (0.088 mole) of PMIDA, respectively. Under stirring, to the mixtures were added dropwise 20.0 g (0.176 mole, 2.0-fold mole/PMIDA) of 30% aqueous hydrogen peroxide at 60 to 65° C. over 3 hours while maintaining said temperature. After the resulting mixtures were allowed to react for 1 hour, crystals were isolated by Isolation method (B) to obtain the results shown in Table 1.

TABLE 1

| Activated carbon | Gross amount obtained (g) | Purity (%) | Net amount obtained (g) | Yield (%) |
| --- | --- | --- | --- | --- |
| (1) PM-KS | 12.52 | 96.1 | 12.03 | 80.8 |
| (2) PC | 13.18 | 97.4 | 12.84 | 86.2 |
| (3) Taiko KW-50 | 13.34 | 95.9 | 12.79 | 85.9 |
| (4) Kuraraycoal PW-W5 | 13.02 | 97.7 | 12.72 | 85.4 |
| (5) Purified Shirasagi | 12.62 | 97.3 | 12.28 | 82.5 |
| (6) NORIT SX-ULTRA | 12.74 | 97.8 | 12.46 | 83.7 |
| (7) NORIT CA-SP | 12.77 | 98.4 | 12.57 | 84.4 |
| (8) NORIT SA-1 | 13.02 | 98.2 | 12.79 | 85.9 |
| (9) DARCO S-51 | 12.59 | 97.5 | 12.28 | 82.5 |
| (10) Calgon Granular AL | 12.75 | 98.2 | 12.52 | 84.1 |
| (11) Taiko SG | 12.88 | 97.8 | 12.60 | 84.6 |
| (12) X-7100 | 12.29 | 95.1 | 11.69 | 78.5 |
| (13) NORIT ROW 0.8 SUPRA | 12.55 | 98.5 | 12.36 | 83.0 |
| (14) NORIT ROX 0.8 | 12.61 | 98.3 | 12.40 | 83.3 |
| (15) DARKO 8x30 | 12.56 | 98.0 | 12.31 | 82.7 |

In the table, (1) in the column of Activated carbon is produced by Mitsui Pharmaceuticals, Inc., (2) is produced by Tsurumi Coal Co., (3) and (11) are produced by Futamura Chemical Industry Co., (4) is produced by Kuraray Chemical Co., (5) and (12) are produced by Takeda Chemical Industries, Ltd., and (6) to (9) and (13) to (15) show products available from Nippon Norit Co.

Example 2

To 100 ml of water were added the activated carbons (products available from Nippon Norit Co.) shown in Table 2 and 20.0 g (0.088 mole) of PMIDA, respectively. Under stirring, to the mixtures were added dropwise 20.0 g (0.176 mole, 2.0-fold mole/PMIDA) of 35% aqueous hydrogen peroxide at 60 to 65° C. over 3 hours while maintaining said temperature. After the resulting mixtures were allowed to react for 15 minutes, crystals were isolated by Isolation method (B) to obtain the results shown in Table 2.

TABLE 2

| Activated carbon | (g) | Gross amount obtained (g) | Purity (%) | Net amount obtained (g) | Yield (%) |
| --- | --- | --- | --- | --- | --- |
| (1) NORIT SA-1 | 1 | 6.72 | 96.0 | 6.45 | 43.3 |
| (2) NORIT SA-1 | 2 | 12.63 | 98.2 | 12.40 | 83.3 |
| (3) NORIT SA-1 | 3 | 12.95 | 98.2 | 12.72 | 85.4 |
| (4) NORIT SA-1 | 4 | 13.08 | 98.0 | 12.82 | 86.1 |
| (5) NORIT SA-1 | 5 | 13.14 | 97.9 | 12.86 | 86.4 |
| (6) NORIT SA-1 | 8 | 13.13 | 97.4 | 12.79 | 85.9 |
| (7) NORIT ROW 0.8 SUPRA | 3 | 12.29 | 95.6 | 11.75 | 78.9 |
| (8) NORIT ROW 0.8 SUPRA | 4 | 12.68 | 98.2 | 12.45 | 83.6 |
| (9) NORIT ROW 0.8 SUPRA | 5 | 12.80 | 98.4 | 12.60 | 84.6 |
| (10) NORIT ROW 0.8 SUPRA | 6 | 12.85 | 97.9 | 12.58 | 84.5 |
| (11) NORIT ROW 0.8 SUPRA | 7 | 12.91 | 98.3 | 12.69 | 85.2 |
| (12) NORIT ROW 0.8 SUPRA | 8 | 12.87 | 98.1 | 12.63 | 84.8 |
| (13) NORIT ROW 0.8 SUPRA | 15 | 12.94 | 97.8 | 12.66 | 85.0 |

Example 3

To 100 ml of water were added 5 g of activated carbon (NORIT ROW 0.8 SUPRA) and 20.0 g (0.088 mole) of PMIDA. Under stirring, to the mixture were added dropwise the 35% aqueous hydrogen peroxides shown in Table 3 at 60 to 65° C. over 3 hours, respectively, while maintaining said temperature. After the resulting mixtures were allowed to react for 1 hour, crystals were isolated by Isolation method (B) to obtain the results shown in Table 3.

TABLE 3

| Hydrogen peroxide (based on mole of PMIDA) | Gross amount obtained (g) | Purity (%) | Net amount obtained (g) | Yield (%) |
| --- | --- | --- | --- | --- |
| (1) 15.0 g, 0.154 mole (1.75 times) | 10.19 | 95.0 | 9.68 | 65.0 |
| (2) 17.1 g, 0.176 mole (2.0 times) | 12.69 | 97.6 | 12.39 | 83.2 |
| (3) 19.3 g, 0.198 mole (2.25 times) | 12.79 | 97.9 | 12.52 | 84.1 |
| (4) 21.4 g, 0.220 mole (2.5 times) | 12.65 | 97.7 | 12.36 | 83.0 |
| (5) 42.8 g, 0.441 mole (5.0 times) | 12.65 | 98.0 | 12.40 | 83.3 |

Example 4

To the amounts of water shown in Table 4 were added 5 g of activated carbon (NORIT ROW 0.8 SUPRA) and 20.0 g (0.088 mole) of PMIDA, respectively. Under stirring, to the mixtures were added dropwise 20.0 g (0.176 mole, 2.0-fold mole/PMIDA) of 30% aqueous hydrogen peroxide at 60 to 65° C. over 3 hours while maintaining said temperature. After the resulting mixtures were allowed to react for 1 hour, crystals were isolated by the isolation methods shown in Table 4, respectively, to obtain the results shown in Table 4.

TABLE 4

| Water | (g) | Isolation method | Gross amount obtained (g) | Purity (%) | Net amount obtained (g) | Yield (%) |
|---|---|---|---|---|---|---|
| (1) | 10 | Stirring was impossible | — | — | — | — |
| (2) | 20 | (B) | 12.26 | 97.9 | 12.00 | 80.6 |
| (3) | 40 | (B) | 12.69 | 97.6 | 12.39 | 83.2 |
| (4) | 100 | (B) | 12.55 | 98.5 | 12.36 | 83.0 |
| (5) | 200 | (B) | 12.53 | 98.4 | 12.33 | 82.8 |
| (6) | 300 | (A) | 12.57 | 98.4 | 12.37 | 83.1 |
| (7) | 400 | (A) | 12.53 | 98.5 | 12.34 | 82.9 |

TABLE 5

| Temperature (° C.) | Gross amount obtained (g) | Purity (%) | Net amount obtained (g) | Yield (%) |
|---|---|---|---|---|
| (1) 25 to 30 | 9.46 | 71.9 | 6.80 | 45.7 |
| (2) 40 to 45 | 10.96 | 76.7 | 8.41 | 56.5 |
| (3) 50 to 55 | 11.53 | 97.7 | 11.26 | 75.6 |
| (4) 60 to 65 | 12.55 | 98.5 | 12.36 | 83.0 |
| (5) 70 to 75 | 12.48 | 98.6 | 12.31 | 82.7 |
| (6) 80 to 85 | 12.39 | 98.6 | 12.22 | 82.1 |
| (7) 90 to 95 | 11.98 | 98.4 | 11.79 | 79.2 |
| (8) Reflux temperature | 6.71 | 98.0 | 6.58 | 44.2 |

Example 6

To the amounts of water shown in Table 6 were added 2 g or 8 g of activated carbon (NORIT SA-1) and 20.0 g (0.088 mole) of PMIDA, respectively. Under stirring, to the mixtures were added dropwise 17.1 g (0.176 mole, 2.0-fold mole/PMIDA) or 19.7 g (0.203 mole, 2.3-fold mole/PMIDA) of 35% aqueous hydrogen peroxide at 60 to 65° C. over 3 hours while maintaining said temperature. After the resulting mixtures were allowed to react for 1 hour, crystals were isolated by Isolation method (B) to obtain the results shown in Table 6.

TABLE 6

| Water (g) | Activated carbon (g) | Hydrogen peroxide | Gross amount obtained (g) | Purity (%) | Net amount obtained (g) | Yield (%) |
|---|---|---|---|---|---|---|
| (1) 40 | 2 | 17.1 g (2.0-fold mole) | 12.78 | 97.2 | 12.40 | 83.3 |
| (2) 40 | 8 | 17.1 g (2.0-fold mole) | 12.89 | 96.8 | 12.48 | 83.8 |
| (3) 40 | 2 | 19.7 g (2.3-fold mole) | 12.75 | 97.5 | 12.43 | 83.5 |
| (4) 40 | 8 | 19.7 g (2.3-fold mole) | 12.77 | 98.0 | 12.51 | 84.0 |
| (5) 200 | 2 | 17.1 g (2.0-fold mole) | 12.47 | 98.2 | 12.25 | 82.3 |
| (6) 200 | 8 | 17.1 g (2.0-fold mole) | 12.60 | 97.7 | 12.31 | 82.7 |
| (7) 200 | 2 | 19.7 g (2.3-fold mole) | 12.48 | 97.9 | 12.22 | 82.1 |
| (8) 200 | 8 | 19.7 g (2.3-fold mole) | 12.62 | 98.2 | 12.39 | 83.2 |

Example 5

To 100 ml of water were added 5 g of activated carbon (NORIT ROW 0.8 SUPRA) and 20.0 g (0.088 mole) of PMIDA. Under stirring, to the mixture were added dropwise 20.0 g (0.176 mole, 2.0-fold mole/PMIDA) of 30% aqueous hydrogen peroxide at the temperatures shown in Table 5 over 3 hours, respectively, while maintaining said temperatures. The reaction time was 8 hours and 30 minutes in the case of employing a reaction temperature of 25 to 30° C. or 1 hour in the case of employing the other reaction temperatures. Thereafter, crystals were isolated by Isolation method (B) to obtain the results shown in Table 5.

Example 7

To the amounts of water shown in Table 7 were added 2 g or 8 g of activated carbon (NORIT SA-1) and 20.0 g (0.088 mole) of PMIDA, respectively. Under stirring, to the mixtures were added dropwise 17.1 g (0.176 mole, 2.0-fold mole/PMIDA) or 19.7 g (0.203 mole, 2.3-fold mole/PMIDA) of 35% aqueous hydrogen peroxide at 80 to 85° C. over 3 hours while maintaining said temperature. After the resulting mixtures were allowed to react for 1 hour, crystals were isolated by Isolation method (B) to obtain the results shown in Table 7.

TABLE 7

| Water (g) | Activated carbon (g) | Hydrogen peroxide | Gross amount obtained (g) | Purity (%) | Net amount obtained (g) | Yield (%) |
|---|---|---|---|---|---|---|
| (1) 40 | 2 | 17.1 g (2.0-fold mole) | 12.82 | 97.8 | 12.54 | 84.2 |
| (2) 40 | 8 | 17.1 g (2.0-fold mole) | 12.76 | 97.4 | 12.43 | 83.5 |
| (3) 40 | 2 | 19.7 g (2.3-fold mole) | 12.84 | 98.0 | 12.58 | 84.5 |
| (4) 40 | 8 | 19.7 g (2.3-fold mole) | 12.85 | 98.1 | 12.61 | 84.7 |
| (5) 200 | 2 | 17.1 g (2.0-fold mole) | 12.64 | 98.3 | 12.43 | 83.5 |
| (6) 200 | 8 | 17.1 g (2.0-fold mole) | 12.66 | 98.4 | 12.46 | 83.7 |
| (7) 200 | 2 | 19.7 g (2.3-fold mole) | 12.62 | 97.8 | 12.34 | 82.9 |
| (8) 200 | 8 | 19.7 g (2.3-fold mole) | 12.74 | 98.2 | 12.51 | 84.0 |

Example 8

(1) The same reaction was carried out 5 times by using only the activated carbon which was used in the reaction (1) of Example 6 and recovered. (2) The same reaction was carried out 10 times by using only the activated carbon which was used in the reaction (2) of Example 6 and recovered. (3) The same reaction was carried out 5 times by using only the activated carbon which was used in the reaction (7) of Example 7 and recovered. (4) The same reaction was carried out 10 times by using only the activated carbon which was used in the reaction (8) of Example 7 and recovered. The respective results are shown in Table 8.

TABLE 8

| | Water (g) | Hydrogen peroxide | Gross amount obtained (g) | Purity (%) | Net amount obtained (g) | Yield (%) |
|---|---|---|---|---|---|---|
| (1) | 40 | 17.1 g (2.0-fold mole) | 12.52 | 98.3 | 12.31 | 82.7 |
| (2) | 40 | 17.1 g (2.0-fold mole) | 12.67 | 98.1 | 12.43 | 83.5 |
| (3) | 200 | 19.7 g (2.3-fold mole) | 12.59 | 98.5 | 12.40 | 83.3 |
| (4) | 200 | 19.7 g (2.3-fold mole) | 12.64 | 98.3 | 12.43 | 83.5 |

In the table, (1) and (3) show the results of the fifth reactions and (2) and (4) show the results of the tenth reactions, respectively.

COMPARATIVE EXAMPLES

Comparative Example 1

To 100 ml of water were added 5.0 g of activated carbon (NORIT SX-ULTRA) and 20.0 g (0.088 mole) of PMIDA. Under stirring, into the mixture was introduced oxygen gas at 60 to 65° C. for 8 hours at a flow rate of 46 ml/min (11.2-fold mole/PMIDA). Then, sodium hydroxide was added to the resulting mixture to form a PMG salt, whereby an aqueous solution of the PMG salt was prepared. The solution was filtered to separate the activated carbon by filtration, and PMG was quantified by HPLC to find that the amount produced was 3.66 g (0.0216 mole)(conversion rate: 24.6%).

Comparative Example 2

A 300 ml pressure glass container was charged with 100 ml of water, 1.5 g of activated carbon (NORIT SX-ULTRA) and 5.0 g (0.022 mole) of PMIDA. Under stirring, into the mixture was introduced air at 60 to 65° C. for 7 hours under pressurization of 5 kg/cm$^2$ at an outlet rate of 15 ml/min. Then, the activated carbon was separated by filtration, and the filtrate was concentrated to 12 ml under reduced pressure to obtain 3.06 g of precipitated crystals (purity: 87.6%, yield: 72.0%).

Comparative Example 3

To 100 ml of water were added 5 g of 5% palladium carbon (produced by Kojima Chemical Co.) and 20.0 g (0.088 mole) of PMIDA. Under stirring, into the mixture was introduced oxygen gas at 60 to 65° C. for 6 hours at a flow rate of 51 ml/min (9.3-fold mole/PMIDA). Then, sodium hydroxide was added to the resulting mixture to form a PMG salt, whereby an aqueous solution of the PMG salt was prepared. The solution was filtered to separate the palladium carbon by filtration, and PMG was quantified by HPLC to find that the amount produced was 0.69 g (0.004 mole) (conversion rate: 4.5%)

Comparative Example 4

A 300 ml pressure glass container was charged with 100 ml of water, 5 g of 5% palladium carbon (produced by Kojima Chemical Co.) and 20.0 g (0.088 mole) of PMIDA. Under stirring, into the mixture was introduced air at 60 to 65° C. for 7 hours under pressurization of 5 kg/cm$^2$ at a flow rate of 20 ml/min. Then, sodium hydroxide was added to the resulting mixture to form a PMG salt, whereby an aqueous solution of the PMG salt was prepared. The solution was filtered to separate the palladium carbon by filtration, and PMG was quantified by HPLC to find that the amount produced was 2.92 g (0.0173 mole)(conversion rate: 19.7%).

Comparative Example 5

To 22 ml of water were added 10.7 g of conc. sulfuric acid and 20.0 g (0.088 mole) of PMIDA. Under stirring, to the mixture were added dropwise 23.9 g (0.211 mole) of 30% aqueous hydrogen peroxide at 90 to 95° C. over 4 hours while maintaining said temperature. The resulting mixture was allowed to react for 1 hour and then cooled to room temperature. Thereafter, 30.2 g of 28% sodium hydroxide was added to the mixture to neutralize the sulfuric acid, and the resulting mixture was cooled to 5° C. to obtain 8.10 g of precipitated crystals (purity: 93.2%, yield: 50.7%).

Comparative Example 6

To 15 ml of water were added 0.31 g of ammonium molybdate and 13.7 g (0.060 mole) of PMIDA. Under stirring, to the mixture were added dropwise 6.0 g (0.062-fold mole) of 35% aqueous hydrogen peroxide at 60 to 65° C. over 15 minutes while maintaining said temperature. The resulting mixture was allowed to react for 50 minutes and then cooled to room temperature. Next, when an aqueous solution obtained by dissolving 0.24 g of sodium pyrosulfite in 5 g of water was added to the above reaction mixture, the resulting mixture was foamed and also the temperature thereof was raised to 65° C. Then, the mixture was cooled to obtain 8.35 g of precipitated crystals (purity: 68.3%, yield: 55.9%).

Comparative Example 7

To 100 ml of water were added 20.0 g (0.088 mole) of PMIDA. Under stirring, to the mixture were added 20.0 g (0.176 mole) of 30% aqueous hydrogem peroxide at 60 to 65° C. over 3 hours while maintaining said temperature. After the resulting mixture was allowed to react for 1 hour, sodium hydroxide was added to the mixture to form a PMG salt, whereby an aqueous solution of the PMG salt was prepared. PMG was quantified by HPLC to find that the amount was 2.7 g (0.0160 mole)(conversion rate: 18.2%).

From Comparative examples described above, the following facts can be indicated.

From Comparative example 1, even when activated carbon is used and oxygen is introduced for a long time (8 hours) under atmospheric pressure, only a small amount of PMG can be obtained.

From Comparative example 2, when activated carbon is used and air is introduced for a long time (7 hours) under pressurization (5 kg/cm$^2$), PMG can be obtained efficiently.

From Comparative example 3, even when palladium carbon is used and oxygen is introduced for a long time (6 hours) under atmospheric pressure, only an extremely small amount of PMG can be obtained.

From Comparative example 4, even when palladium carbon is used and air is introduced for a long time (7 hours) under pressurization (5 kg/cm$^2$), only a small amount of PMG can be obtained.

From Comparative example 5, even when reaction is carried out by using hydrogen peroxide and conc. sulfuric acid under atmospheric pressure, yield of PMG is low.

From Comparative example 6, when reaction is carried out by using hydrogen peroxide, molybdenum and sodium pyrosulfite under atmospheric pressure, the reaction mixture is foamed vigorously, and the temperature thereof is increased, thereby the reaction can be controlled with diffuculty, and the yield of PMG is low.

From Comparative example 7, when PMIDA is reacted with hydrogen peroxide under atmospheric pressure, only a small amount of PMG can be obtained.

As compared with the prior art, the process of the present invention can be carried out under atmospheric pressure, so that pressure equipment is not required. Since no acid is used, there is no such problem as corrosion of the reaction apparatus, and since a metal compound in which a harmful compound might be contained is not used as a catalyst, there is not required intricate disposal for such a compound, and the process of the present invention can be carried out safely. It is easy to control the reaction, and the used activated carbon can be recycled any number of times without regeneration treatment. The desired compound of the present invention can be obtained in good purity and yield, and the process of the present invention is suitable as an industrial preparation process.

What is claimed is:

1. A process for preparing a N-phosphonomethylglycine, which comprises contacting N-phosphonomethyliminodiacetic acid with water, activated carbon and hydrogen peroxide.

2. The process according to claim 1, wherein the hydrogen peroxide is in an amount of at least 2 moles based on 1 mole of the N-phosphonomethyliminodiacetic acid and the activated carbon is in an amount of 0.1 part by weight based on 1 part by weight of the N-phosphonomethyliminodiacetic acid.

3. The process according to claim 2, wherein the hydrogen peroxide is in an amount of 2 to 5 moles based on 1 mole of the N-phosphonomethyliminodiacetic acid.

4. The process according to claim 2, wherein the hydrogen peroxide is in an amount of 2.0 to 2.5 moles based on 1 mole of the N-phosphonomethyliminodiacetic acid.

5. The process according to claim 2, wherein the activated carbon is in an amount of 0.1 to 0.75 part by weight based on 1 part by weight of the N-phosphonomethyliminodiacetic acid.

6. The process according to claim 2, wherein the activated carbon is in an amount of 0.1 to 0.4 part by weight based on 1 part by weight of the N-phosphonomethyliminodiacetic acid.

7. The process according to claim 2, wherein the activated carbon comprises activated carbon which is recovered from the process.

8. The process according to claim 2, wherein said process is carried out under atmospheric pressure.

9. The process according to claim 4, wherein the activated carbon is in an amount of 0.1 to 0.4 part by weight based on 1 part by weight of the N-phosphonomethyliminodiacetic acid.

10. The process according to claim 9, wherein the water is in an amount of 2 to 10 parts by weight based on 1 part by weight of the N-phosphonomethyliminodiacetic acid.

11. The process according to claim 10, wherein said process is carried out for 30 minutes to 4 hours.

12. A process for preparing N-phosphonomethylglycine, which comprises adding hydrogen peroxide to N-phosphonomethyliminodiacetic acid, water and activated carbon under heating and agitating.

13. The process according to claim 12, wherein the hydrogen peroxide is in an amount of at least 2 moles based on 1 mole of the N-phosphonomethyliminodiacetic acid and the activated carbon is in an amount of at least 0.1 part by weight based on 1 part by weight of the N-phosphonomethyliminodiacetic acid.

14. The process according to claim 13, wherein the heating is carried out at a temperature of above 30° C.

15. The process according to claim 13, wherein the heating is carried out at a temperature of 50 to 90° C.

16. The process according to claim 13, wherein the heating is carried out at a temperature of 60 to 80° C.

17. The process according to claim 14, wherein the hydrogen peroxide is in an amount of 2 to 5 moles based on 1 mole of the N-phosphonomethyliminodiacetic acid.

18. The process according to claim 14, wherein the hydrogen peroxide is in an amount of 2 to 2.5 moles based on 1 mole of the N-phosphonomethyliminodiacetic acid.

19. The process according to claim 14, wherein the activated carbon is in an amount of 0.1 to 0.75 part by weight based on 1 part by weight of the N-phosphonomethyliminodiacetic acid.

20. The process according to claim 14, wherein the activated carbon is in an amount of 0.1 to 0.4 part by weight based on 1 part by weight of the N-phosphonomethyliminodiacetic acid.

21. The process according to claim 14, wherein the activated carbon comprises activated carbon which is recovered from the process.

22. The process according to claim 14, wherein said process is carried out under atmospheric pressure.

23. The process according to claim 22, wherein the water is in an amount of 2 to 10 parts by weight based on 1 part by weight of the N-phosphonomethyliminodiacetic acid.

24. The process according to claim 23, wherein said process is carried out for 30 minutes to 4 hours.

25. The process according to claim 16, wherein the hydrogen peroxide is in an amount of 2 to 2.5 moles based on 1 mole of the N-phosphonomethyliminodiacetic acid; the activated carbon is in an amount of 0.1 to 0.4 part by weight based on 1 part by weight of the N-phosphonomethyliminodiacetic acid; and the water is in an amount of 2 to 10 parts by weight based on 1 part by weight of the N-phosphonomethyliminodiacetic acid.

26. The process of claim 1, wherein the hydrogen peroxide is in the form of a 30 to 60% by weight hydrogen peroxide aqueous solution.

27. The process of claim 13, wherein the hydrogen peroxide is in the form of a 30 to 60% by weight hydrogen peroxide aqueous solution.

28. The process of claim 25, wherein the hydrogen peroxide is in the form of a 30 to 60% by weight hydrogen peroxide aqueous solution.

* * * * *